United States Patent [19]

Ziemniak et al.

[11] Patent Number: 6,010,685
[45] Date of Patent: Jan. 4, 2000

[54] SKIN PROTECTANT COMPRISING 5-SUBSTITUTED AND 5,5-DISUBSTITUTED 3,4-DIHYDROXY-2(5H)-FURANONES

[75] Inventors: John A. Ziemniak, Gwynedd Valley, Pa.; Allen T. Hopper, Somerset, N.J.; Peter T. Pugliese, Reading, Pa.

[73] Assignee: Oxis International, Inc., Portland, Oreg.

[21] Appl. No.: 09/264,659

[22] Filed: Mar. 8, 1999

[51] Int. Cl.[7] .............................. A61K 7/42; A61K 7/00; A61K 31/34
[52] U.S. Cl. .............................. 424/59; 424/60; 424/400; 424/401; 514/473
[58] Field of Search ................................ 424/59, 60, 400, 424/401; 514/473

[56] References Cited

U.S. PATENT DOCUMENTS 4,426,380  1/1984  Wenk et al. .............................. 424/244

*Primary Examiner*—Shelley A. Dodson
*Attorney, Agent, or Firm*—Klauber & Jackson

[57] ABSTRACT

Formulations of racemic or optically active 3,4-dihydroxy-5-aryl-2(5H)-furanones are provided for topical administration to the skin for the inhibition and prevention of sunburn cell formation resulting from exposure to ultraviolet radiation and other sources of damage, and for the treatment of skin aging. The compounds may be formulated in combination with a sunscreen, and may be applied before, during, and/or after exposure.

27 Claims, No Drawings

SKIN PROTECTANT COMPRISING 5-SUBSTITUTED AND 5,5-DISUBSTITUTED 3,4-DIHYDROXY-2(5H)-FURANONES

BACKGROUND OF THE INVENTION

Protection of the skin from the deleterious effects of ultraviolet light (UV) exposure and other radiation sources prevents the deterioration in the appearance and elasto-mechanical properties of the skin that accompany long-term exposure. The perceived enhanced physical appearance of the skin provided acutely by suntanning is unfortunately offset by the chronic structural deterioration of the skin often leading over time to adversely-perceived skin pigmentation and wrinkling, as well as dysproliferative changes in the skin leading to neoplasia including basal cell and squamous cell carcinoma, and melanoma. It is well known that chronic exposure to the sun results in a deeply grooved and thickened skin, undesirable attributes for which prophylactic and treatment modalities are sought by susceptible individuals. In short, sunlight prematurely ages the skin.

An acute effect of UV damage to the skin is manifest by the necrosis of keratinocytes resulting in the appearance of dyskeratotic cells within the epidermis known as sunburn cells (Daniels et al., 1961, J. Invest. Dermatol. 37:351–7; Gilchrest et al., 1981, J. Amer. Acad. Dermatol. 5:411–22). In addition to UV exposure, numerous other sources of damage to the skin occur in the environment, including exposure to chemicals including airborne industrial and other pollutants, ionizing radiation, among others. Means to protect the aforementioned sequelae of such exposure is highly desirable to prevent the premature aging of the skin.

Certain agents have been shown to reduce the number of sunburn cells after exposure to UV radiation, among them α-tocopherol (Ritter et al., 1997, Plast. Reconstr. Surg. 100:973–80) and zinc (Record et al., 1996, Biol. Trace Elem. Res. 53:19–25). Such agents offer protection to the skin from the deleterious effects of UV radiation.

It is toward the development of an effective composition for protecting the skin from such damage and prevent premature skin aging that the present application is directed.

The citation of any reference herein should not be construed as an admission that such reference is available as "Prior Art" to the instant application.

SUMMARY OF THE INVENTION

In accordance with the present invention, methods are provided for reducing the formation of sunburn cells in mammalian skin, comprising applying to said skin a topical formulation comprising an effective amount of a racemic or optically active compound of the following formula:

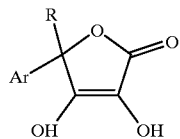

wherein Aryl is a substituted or unsubstituted aryl group, R is hydrogen, phenyl or lower alkyl; or a pharmaceutically acceptable salt thereof. The aryl group may be for example, phenyl, biphenyl, naphthyl, quinolinyl, which may be further substituted, for example, by a halo, aryl, alkyl, alkoxy, hydroxy, or alkylthio group. Preferably, the aryl group is a phenyl or biphenyl, or substituted phenyl or biphenyl, such as 1,1'-biphenyl, 4-chlorophenyl, 2-methylpropylphenyl, or a 4-chlorobiphenyl group. The compound may be a racemic mixture or optically active form.

Non-limiting examples of compounds useful for the present invention wherein R is H include racemic or optically active 3,4-dihydroxy-5-(4'-biphenyl)-2(5H)-furanone; 3,4-dihydroxy-5-(4'-methylpropylphenyl)-2(5H)-furanoe; 3,4-dihydroxy-5-(4'-chlorophenyl)-2(5H)-furanone; and 3,4-dihydroxy-5-(4"-chlorobiphenyl)-2(5H)-furanone. Examples of compounds wherein R is phenyl or alkyl include racemic or optically active 3,4-dihydroxy-5-(4'-biphenyl)-5-methyl-2(5H)-furanone; 3,4-dihydroxy-5-(4'-chlorophenyl)-5-methyl-2(5H)-furanone; 3,4-dihydroxy-5-(4'-methylpropylphenyl)-5-methyl-2(5H)-furanone; and 3,4-dihydroxy-5-(4"-chlorobiphenyl)-5-methyl-2(5H)-furanone. The compound preferably may comprise from about 1% to 10% of a topically-acceptable formulation.

In a further embodiment of the present invention, method are provided for inhibiting the formation of sunburn cells in skin after skin is exposed to ultraviolet radiation, comprising applying to the skin a composition including a sunburn cell formation protective amount of a racemic or optically active compound of the following formula:

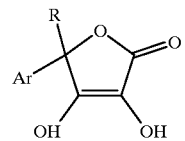

wherein Aryl and R, and examples thereof, are as defined hereinabove.

In a further embodiment of the present invention, a method is provided for preventing and/or reducing the appearance of skin changes associated with aging resulting from exposure to ultraviolet radiation, comprising applying to the skin a composition comprising an effective amount of a racemic or optically active compound of the following formula:

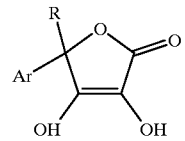

wherein Aryl and R, and examples thereof, are as defined hereinabove.

In a further embodiment of the present invention, the composition comprising the racemic or optically active 5-substituted or 5,5-disubstituted 3,4-dihydroxy-2(5H)-furanone formulation described herein may further include a sunscreen.

In a still further embodiment, methods of the present invention may include a sunscreen within the formulation comprising the racemic or optically active 5-substituted 3,4-dihydroxy-2(5H)-furanone.

These and other aspects of the present invention will be better appreciated by reference to the following Detailed Description.

DETAILED DESCRIPTION OF THE INVENTION

The term "substituted or unsubstituted aryl", as utilized herein, means an aromatic or heteroaromatic group which can be optionally substituted by one or more lower alkyl, lower alkenyl, lower alkynyl, loweralkylthio, loweralkylsulfonyl, loweralkylsulfonylamino, aromatic or heteroaromatic groups. Examples of unsubstituted aryl groups include phenyl, pyridyl, biphenyl, thiophenyl, furyl, pyrrolyl and the like. Examples of substituents include halo, aryl, alkyl, alkoxy, hydroxy, or alkylthio groups. Thus, substituted aryl groups include those such as alkyl-substituted aryl, e.g., tolyl, 3-methylpyridyl, 2,3-dimethylphenyl, 4-ethylphenyl, 4-isobutylphenyl; alkoxy-substituted aryl, e.g, 4-methoxyphenyl-; loweralkylthio- or loweralkylsulfonyl-substituted aryl, e.g., 1-propylthiophenyl, 1-pentylsulfonylphenyl, lower alkenyl substituted phenyl, e.g., 4-(2-(2Z-hexenyl]) phenyl and aryl-substituted aryl, e.g., 1,1'-biphenyl and naphthyl. Preferred compounds include aryl-substituted phenyl groups, such as wherein aryl is 1,1'-biphenyl. Complex aryl groups such as those derived from flavone, dibenzofuran, 1,8-naphthalimide, 1,8-naphtholsultam, quinoline, 4,5-diphenyl-2-thio-1, 3-isoxazole, and napthalenethiol can also be utilized as substituent groups. Further halo, aryl, alkyl, alkoxy, hydroxy, or alkylthio substitutions of the aryl substituent are also contemplated, such as, for example, the 4-chlorobiphenyl compound referred to above.

The compounds of the present invention can be used as mixtures of enantiomers, as well as optically active isomers, due to the asymmetric carbon atoms of the ring structure and the double bonds present in the substituents. The present invention contemplates the use of both the individual isomers, as well as the racemic or cis/trans mixtures or both.

In accordance with the present invention, methods are provided for reducing the formation of sunburn cells in mammalian skin, comprising applying to said skin a topical formulation comprising an effective amount of a racemic or optically active compound of the following formula:

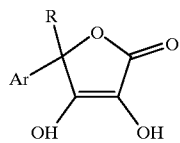

wherein Aryl is a substituted or unsubstituted aryl group, R is hydrogen, phenyl or lower alkyl; or a pharmaceutically acceptable salt thereof. The aryl group may be for example, phenyl, biphenyl, naphthyl, quinolinyl, which may be further substituted, for example, by a halo, aryl, alkyl, alkoxy, hydroxy, or alkylthio group. Preferably, the aryl group is a phenyl or biphenyl, or substituted phenyl or biphenyl, such as 1,1'-biphenyl, 4-chlorophenyl, 2-methylpropylphenyl, or a 4-chlorobiphenyl group. The compound may be a racemic mixture or optically active form.

Non-limiting examples of compounds useful for the present invention wherein R is H include racemic or optically active 3,4-dihydroxy-5-(4'-biphenyl)-2(5H)-furanone; 3,4-dihydroxy-5-(4'-methylpropylphenyl)-2(5H)-furanone; 3,4-dihydroxy-5-(4'-chlorophenyl)-2(5H)-furanone; and 3,4-dihydroxy-5-(4"-chlorobiphenyl)-2(5H)-furanone. Examples of compounds wherein R is phenyl or alkyl include racemic or optically active 3,4-dihydroxy-5-(4'-biphenyl)-5-methyl-2(5H)-furanone; 3,4-dihydroxy-5-(4'-chlorophenyl)-5-methyl-2(5H)-furanone; 3,4-dihydroxy-5-(4'-methylpropylphenyl)-5-methyl-2(5H)-furanone; and 3,4-dihydroxy-5-(4'-chlorobiphenyl)-5-methyl-2(5H)-furanone. The compound preferably may comprise from about 1% to 10% of a topically-acceptable formulation.

In a further embodiment of the present invention methods are provided for inhibiting the formation of sunburn cells in skin after skin is exposed to ultraviolet radiation, comprising applying to the skin a composition including a sunburn cell formation protective amount a racemic or optically active compound of the following formula:

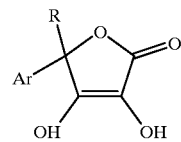

wherein Aryl is a substituted or unsubstituted aryl group, R is hydrogen, phenyl or lower alkyl; or a pharmaceutically acceptable salt thereof. The aryl group may be for example, phenyl, biphenyl, naphthyl, quinolinyl, which may be further substituted, for example, by a halo, aryl, alkyl, alkoxy, hydroxy, or alkylthio group. Preferably, the aryl group is a phenyl or biphenyl, or substituted phenyl or biphenyl, such as 1,1'-biphenyl, 4-chlorophenyl, 2-methylpropylphenyl, or a 4-chlorobiphenyl group. The compound may be a racemic mixture or optically active form.

Non-limiting examples of compounds useful for the present invention wherein R is H include racemic or optically active 3,4-dihydroxy-5-(4'-biphenyl)-2(5H)-furanone; 3,4-dihydroxy-5-(4'-methylpropylphenyl)-2(5H)-furanone; 3,4-dihydroxy-5-(4'-chlorophenyl)-2(5H)-furanone; and 3,4-dihydroxy-5-(4"-chlorobiphenyl)-2(5H)-furanone. Examples of compounds wherein R is phenyl or alkyl include racemic or optically active 3,4-dihydroxy-5-(4'-biphenyl)-5-methyl-2(5H)-furanone; 3,4-dihydroxy-5-(4'-chlorophenyl)-5-methyl-2(5H)-furanone; 3,4-dihydroxy-5-(4'-methylpropylphenyl)-5-methyl-2(5H)-furanone; and 3,4-dihydroxy-5-(4'-chlorobiphenyl)-5-methyl-2(5H)-furanone. The compound preferably may comprise from about 1% to 10% of a topically-acceptable formulation.

In a further embodiment of the present invention, methods are provided for preventing and/or reducing the appearance of skin changes associated with aging resulting from exposure to ultraviolet radiation, comprising applying to the skin a composition comprising an effective amount a racemic or optically active compound of the following formula:

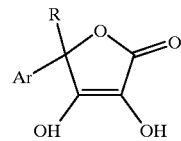

wherein Aryl is a substituted or unsubstituted aryl group, R is hydrogen, phenyl or lower alkyl; or a pharmaceutically acceptable salt thereof. The aryl group may be for example, phenyl, biphenyl, naphthyl, quinolinyl which may be further substituted, for example, by a halo, aryl, alkyl, alkoxy, hydroxy, or alkylthio group. Preterably, the aryl group is a phenyl or biphenyl, or substituted phenyl or biphenyl, such as 1,1'-biphenyl, 4-chlorophenyl, 2-methylpropylphenyl, or a 4-chlorobiphenyl group. The compound may be a racemic mixture or optically active form.

Non-limiting examples of compounds useful for the present invention wherein R is H include racemic or optically active 3,4-dihydroxy-5-(4'-biphenyl)-2(5H)-furanone; 3,4-dihydroxy-5-(4'-methylpropylphenyl)-2(5H)-furanone; 3,4-dihydroxy-5-(4'-chlorophenyl)-2(5H)-furanone; and 3,4-dihydroxy-5-(4"-chlorobiphenyl)-2(5H)-furanone. Examples of compounds wherein R is phenyl or alkyl include racemic or optically active 3,4-dihydroxy-5-(4'- biphenyl)-5-methyl-2(5H)-furanone; 3,4-dihdroxy-5-(4'-chlorophenyl)-5-methyl-2-(5H)-furanone; 3,4-dihydroxy-5-(4'-methylpropylphenyl-5-methyl-2(5H)-furanone; and 3,4-dihydroxy-5-(4''-chlorobiphenyl)-5-methyl-2(5H)-furanone. The compound preferably may comprise from about 1% to 10% of a topically-acceptable formulation.

In a further embodiment of the present invention, the composition comprising the racemic or optically active 5-substituted or 5,5-disubstituted 3,4-dihydroxy-2(5H)-furanone formulation described herein may further include a sunscreen, for example, p-aminobenzoic acid and related compounds, or other sunscreens known to the skilled artisan, and combinations thereof.

As an example of the compounds of the present invention, racemic or optically active 4-(4-biphenyl)-2-hydroxytetronic acid or 5-[(1,1'-biphenyl)-4-yl]-3,4-dihydroxy-2(5H)-furanone, herein abbreviated BPHTA, has been previously used as an inhibitor of ADP-induced and arachidonic acid-induced platelet aggregation, as a cyclooxygenase inhibitor, and an inhibitor of prostaglandin H synthase (Witiak et al., 1992, Trends in Medicinal Chemistry. Proceedings of the XI Int. Symp. Med. Chem., Sarel et al., eds., Blackwell Scientific Publications, Oxford, pp. 243–256; U.S. Pat. No. 5,504,108). In one study, the compound has been shown to enhance lymphokine-activated killer activity of peripheral blood mononuclear cells (Witiak et al., 1993, Proc. Amer. Soc. Cancer Res. 34:447) but in other studies showed a less modest effect (Triozzi et al., 1993, Int. J. Immunopharmacology 15:47–54; U.S. Pat. No. 5,071,872). In U.S. Pat. No. 5,504,108, the (S)-(+) and (R)-(−) enantiomers have been shown to inhibit arachidonic acid-induced platelet aggregation as well as enhance TNF and tissue factor production from human monocytes (U.S. Pat. No. 5,504,108). Synthesis of the enantiomers is also described in U.S. Pat. Nos. 5,504,108 and 5,399,721. All of these citations are incorporated herein by reference in their entireties.

It was found unexpectedly and by surprise that BPHTA exhibits the beneficial property of protecting skin from the damaging effects of ultraviolet light by reducing the appearance of sunburn cells. A topical formulation of the compounds of the present invention are thus useful for protecting skin from UV damage but also from other sources of damage to skin. Such formulations may be applied to the skin before, during, or after exposure to the source of UV or other source of damage. The compounds of the present invention also have general utility in the prevention in the appearance of the effects of aging on the skin.

The compounds of the present invention, either the racemate, the enantiomers, or various combinations of the enantiomers, may be synthesized by known methods as described in the citations above, and prepared as a topical formulation for application to the skin. Various topically-acceptable formulations are known to the skilled artisan which can serve as a suitable carrier for the compound of the present invention. It can be readily appreciated that a transdermal route of administration may be enhanced by use of a dermal penetration enhancer, e.g., such as enhancers described in U.S. Pat. No. 5,164,189 (supra), U.S. Pat. No. 5,008,110 (supra), and U.S. Pat. No. 4,879,119, issued Nov. 7, 1989 to Aruga et al., the disclosure of each of which is incorporated herein by reference in its entirety. It may also be formulated by encapsulation into a liposome for topical administration.

Examples of compounds useful in the compositions of the present invention include racemic or optically active:

3,4-dihydroxy-5-(4'-biphenyl)-2(5H)-furanone 3,4-dihydroxy-5-(4'-methylpropylphenyl)-2(5H)-furanone 3,4-dihydroxy-5-(4'-chlorophenyl)-2(5H)-furanone 3,4-dihydroxy-5-(4''-chlorobiphenyl)-2(5H)-furanone 3,4-dihydroxy-5-(4'-biphenyl)-5-methyl-2(5H)-furanone 3,4-dihydroxy-5-(4'-chlorophenyl)-5-methyl-2(5H)-furanone 3,4-dihydroxy-5-(4'-methylpropylphenyl)-5-methyl-2(5H)-furanone, and 3,4-dihydroxy-5-(4''-chlorobiphenyl)-5-methyl-2(5H)-furanone.

Procedures for the synthesis of the compounds of the present invention may be found in U.S. Pat. Nos. 5,504,108, 5,399,724, 5,298,526, 5,095,126, 5,399,721, WO 98/07714, and other citations herein, which are incorporated by reference in their entireties.

In a further embodiment of the present invention, the compositions of the present invention may further contain a sunscreen. Inclusion of a sunscreen reduces the amount of ultraviolet radiation impacting the cells of the skin, reducing the deleterious effects of UV. With a sunscreen, the level of the compound of the present invention in a formulation may be lowered. The levels of sunscreen and furanone compound may be adjusted by the skilled artisan to provide a balance between efficacy and any potential toxicity of the furanone, as well as efficacy and toxicity of the sunscreen. Inclusion of the sunscreen in a formulation would be of particular benefit for application to the skin prior or during exposure to UV or other sources of actinic radiation.

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE

Male and female hairless mice of at least 8 weeks old were used in the study. The mice were conditioned in the laboratory for one to two weeks, maintained on regular mouse chow ad lib, and subjected to a 24-hour day/night cycle.

BPHTA was prepared as a formulation in a mixture of 50% oleic acid and 50% SD39 (denatured ethanol). Formulations containing 1% BPHTA and 2.5% BPHTA were prepared. The test compositions were swabbed over the entire backs of the mice. Two mice were used for each test composition; two mice untreated before UV irradiation served as controls. One hour after application, the mice were placed in a special cage for irradiation, which preventions the mice from climbing but allows them to move on a plane. Ultraviolet lamps 40 inches in length, emitting UVB, were used to supply the UV energy. The mice were exposed to UVB for 1.75 minutes for a dose of 70 mj/cm$^2$, and then sacrificed 24 hours later by cervical dislocation. The skin was removed and processed for histological staining (hematoxylin & eosin). Sunburn cells were counted by two independent researchers using 400×power on an Olympus microscope. Twenty fields were counted for each slide.

The results are shown in Table 1.

TABLE 1

| Test Group | Sunburn cells/20 fields | Percent reduction |
|---|---|---|
| Control | 104 | — |
| 1% 153 | 72 | 31% |
| 2.5% 153 | 32 | 69% |

These data demonstrate the effectiveness of BPHTA in reducing the extent of sunburn cells in the skin of UVB-irradiated mice.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

Various publications are cited herein, the disclosures of which are incorporated by reference in their entireties.

What is claimed is:

1. A method for reducing the formation of sunburn cells in mammalian skin, comprising applying to said skin a topical formulation comprising an effective amount of a racemic or optically active compound of the following formula:

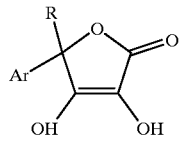

wherein Aryl is a substituted or unsubstituted aryl group, R is hydrogen, phenyl or lower alkyl; or a pharmaceutically acceptable salt thereof.

2. The method of claim 1 wherein said aryl group may be selected from the group consisting of phenyl, biphenyl, naphthyl, and quinolinyl.

3. The method of claim 2 wherein said aryl group is optionally further substituted by a substituent selected from the group consisting of halo, aryl, alkyl, alkoxy, hydroxy, and alkylthio.

4. The method of claim 3 wherein R is hydrogen.

5. The method of claim 4 wherein said compound is selected from the group consisting of racemic or optically active 3,4-dihydroxy-5-(4'-biphenyl)-2(5H)-furanone; 3,4-dihydroxy-5-(4'-methylpropylphenyl)-2(5H)-furanone; 3,4-dihydroxy-5-(4'-chlorophenyl)-2(5H)-furanone; and 3,4-dihydroxy-5-(4"-chlorobiphenyl)-2(5H)-furanone.

6. The method of claim 3 wherein R is an alkyl group.

7. The method of claim 6 wherein said compound is selected from the group consisting of racemic or optically active 3,4-dihydroxy-5-(4'-biphenyl)-5-methyl-2(5H)-furanone; 3,4-dihydroxy-5-(4'-chlorophenyl)-5-methyl-2(5H)-furanone; 3,4-dihydroxy-5-(4'-methylpropylphenyl)-5-methyl-2(5H)-furanone; and 3,4-dihydroxy-5-(4"-chlorobiphenyl)-5-methyl-2(5H)-furanone.

8. The method of claim 7 wherein said compound is racemic or optically active 3,4-dihydroxy-5-(4'-biphenyl)-2(5H)-furanone.

9. The method of claim 1 wherein said formulation additionally comprises a sunscreen.

10. A method for inhibiting the formation of sunburn cells in skin after skin is exposed to ultraviolet radiation comprising applying to the skin a composition comprising an effective amount of a racemic or optically active compound of the following formula:

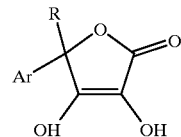

wherein Aryl is a substituted or unsubstituted aryl group, R is hydrogen, phenyl or lower alkyl; or a pharmaceutically acceptable salt thereof.

11. The method of claim 10 wherein said aryl group may be selected from the group consisting of phenyl, biphenyl, naphthyl, and quinolinyl.

12. The method of claim 11 wherein said aryl group is optionally further substituted by a substituent selected from the group consisting of halo, aryl, alkyl, alkoxy, hydroxy, and alkylthio.

13. The method of claim 12 wherein R is hydrogen.

14. The method of claim 13 wherein said compound is selected from the group consisting of racemic or optically active 3,4-dihydroxy-5-(4'-biphenyl)-2(5H)-furanone; 3,4-dihydroxy-5-(4'-methylpropylphenyl)-2(5H)-furanone; 3,4-dihydroxy-5-(4'-chlorophenyl)-2(5H)-furanone; and 3,4-dihydroxy-5-(4"-chlorobiphenyl)-2(5H)-furanone.

15. The method of claim 12 wherein R is an alkyl group.

16. The method of claim 15 wherein said compound is selected from the group consisting of racemic or optically active 3,4-dihydroxy-5-(4'-biphenyl)-5-methyl-2(5H)-furanone; 3,4-dihydroxy-5-(4'-chlorophenyl)-5-methyl-2(5H)-furanone; 3,4-dihydroxy-5-(4'-methylpropylphenyl)-5-methyl-2(5H)-furanone; and 3,4-dihydroxy-5-(4"-chlorobiphenyl)-5-methyl-2(5H)-furanone.

17. The method of claim 10 wherein said compound is racemic or optically active 3,4-dihydroxy-5-(4'-biphenyl)-2(5H)-furanone.

18. The method of claim 10 wherein said formulation additionally comprises a sunscreen.

19. A method for preventing and/or reducing the appearance of skin changes associated with aging resulting from exposure to ultraviolet radiation, comprising applying to the skin a composition comprising an effective amount a racemic or optically active compound of the following formula:

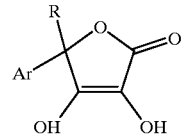

wherein Aryl is a substituted or unsubstituted aryl (group, R is hydrogen, phenyl or lower alkyl; or a pharmaceutically acceptable salt thereof.

20. The method of claim 19 wherein said aryl group may be selected from the group consisting of phenyl, biphenyl, naphthyl, and quinolinyl.

21. The method of claim 20 wherein said aryl group is optionally further substituted by a substituent selected from the group consisting of halo, aryl, alkyl, alkoxy, hydroxy, and alkylthio.

22. The method of claim 21 wherein R is hydrogen.

23. The method of claim 22 wherein said compound is selected from the group consisting of racemic or optically active 3,4-dihydroxy-5-(4'-biphenyl)-2(5H)-furanone; 3,4- dihydroxy-5-(4'-methylpropylphenyl)-2(5H)-furanone; 3,4-dihydroxy-5-(4'-chlorophenyl)-2(5H)-furanone; and 3,4-dihydroxy-5-(4"-chlorobiphenyl)-2(5H)-furanone.

24. The method of claim 21 wherein R is an alkyl group.

25. The method of claim 24 wherein said compound is selected from the group consisting of racemic or optically active 3,4-dihydroxy-5-(4'-biphenyl)-5-methyl-2(5H)-furanone; 3,4-dihydroxy-5-(4'-chlorophenyl)-5-methyl-2(5H)-furanone; 3,4-dihydroxy-5-(4'-methylpropylphenyl)-5-methyl-2(5H)-furanone; and 3,4-dihydroxy-5-(4"-chlorobiphenyl)-5-methyl-2(5H)-furanone.

26. The method of claim 19 wherein said compound is racemic or optically active 3,4-dihydroxy-5-(4'-biphenyl)-2(5H)-furanone.

27. The method of claim 19 wherein said formulation additionally comprises a sunscreen.

* * * * *